(12) United States Patent
Lavallée et al.

(10) Patent No.: US 6,658,921 B2
(45) Date of Patent: Dec. 9, 2003

(54) TESTING PROCESS AND APPARATUS FOR DETERMINING ABSORPTION PROPERTIES OF POROUS SPECIMEN

(75) Inventors: Paul Lavallée, Verchères (CA); Michel Küntz, Montréal (CA)

(73) Assignee: Universite du Quebec a Montreal, Montreal (CA)

( * ) Notice: Subject to any disclaimer, the term of this patent is extended or adjusted under 35 U.S.C. 154(b) by 40 days.

(21) Appl. No.: 10/104,971

(22) Filed: Mar. 22, 2002

(65) Prior Publication Data

US 2002/0162387 A1 Nov. 7, 2002

(51) Int. Cl.$^7$ ............................ G01N 5/02; G01G 19/52
(52) U.S. Cl. ............................................ 73/73; 177/50
(58) Field of Search ..................... 73/38, 73, 864.71, 73/863.01, 866, 864.72; 177/50

(56) References Cited

U.S. PATENT DOCUMENTS

| | | | |
|---|---|---|---|
| 2,886,964 A | 5/1959 | Shapiro et al. | 73/38 |
| 2,913,658 A | 11/1959 | Burdine | 324/5 |
| 3,248,930 A | 5/1966 | Speegle et al. | 73/38 |
| 3,641,823 A * | 2/1972 | Harris et al. | 37/310 |
| 3,683,674 A | 8/1972 | Roy | 73/38 |
| 3,702,564 A * | 11/1972 | Chenevert | 34/265 |
| 3,766,671 A * | 10/1973 | Guntert | 34/412 |
| 3,858,329 A * | 1/1975 | Koide et al. | 211/45 |
| 3,882,714 A | 5/1975 | Libal et al. | 73/38 |
| 4,176,464 A * | 12/1979 | Randolph | 73/864.81 |
| 4,308,028 A * | 12/1981 | Elkins | 34/493 |
| 4,355,535 A | 10/1982 | Vaughan | 73/37.8 |
| 4,381,665 A | 5/1983 | Levine et al. | 73/73 |
| 4,446,973 A * | 5/1984 | Fuller et al. | 34/536 |
| 4,982,616 A * | 1/1991 | Koch et al. | 73/864.81 |
| 5,063,791 A * | 11/1991 | Martin | 73/864.31 |
| 5,146,692 A * | 9/1992 | Ogiri et al. | 34/380 |
| 5,219,388 A | 6/1993 | Meletiou et al. | 73/155 |
| 5,299,140 A | 3/1994 | Ankeny et al. | 364/497 |
| 5,325,604 A * | 7/1994 | Little | 34/493 |
| 5,425,265 A | 6/1995 | Jaisinghani | 73/38 |
| 5,535,616 A | 7/1996 | Bors et al. | 73/38 |
| 5,569,839 A | 10/1996 | Ajot et al. | 73/38 |
| 5,679,885 A | 10/1997 | Lenormand et al. | 73/38 |
| 5,844,136 A | 12/1998 | Marsala et al. | 73/38 |
| 5,858,791 A | 1/1999 | Lemaire | 436/25 |
| 5,970,783 A * | 10/1999 | Levie et al. | 73/73 |
| 5,983,708 A | 11/1999 | Mayer et al. | 73/38 |
| 6,141,888 A * | 11/2000 | Cammarata | 34/536 |

OTHER PUBLICATIONS

"Standard Test Methods for Sampling and Testing Brick and Structural Clay Tile" ASTM, 2000, C–67–99a, 1–10.
"Water sorptivity of mortars and concretes: a review", C. Hall (1989), Magazine of Concrete Research, 41, 51–61.

(List continued on next page.)

Primary Examiner—Daniel S. Larkin
Assistant Examiner—Katina Wilson
(74) Attorney, Agent, or Firm—Myers Bigel Sibley & Sajovec, PA (57) ABSTRACT

Testing process and apparatus for determining absorption properties of a porous specimen. The porous specimen is brought in a predetermined state of contact with the body of water held by a reservoir, for inducing water absorption in the porous specimen. A weight of the porous specimen is monitored for a predetermined time period once the contact is established to produce weight data over time. The predetermined state of contact is maintained substantially constant during the time period by permanent circulation of water in the reservoir. The absorption properties of the porous specimen are determined as a function of the weight data over time.

26 Claims, 4 Drawing Sheets

OTHER PUBLICATIONS

"*Barrier performance of concrete: A review of fluid transport theory*", C. Hall (1994), Material and structures, 1994, 27, 291–306.

"*A water sorptivity test for mortar and concrete*", B.B. Sabir et al., 1998, Materials and structures, 31, 568–574.

"*Experimental evidence and theoretical analysis of anomalous diffusion during water infiltration in porous building materials*", Michel Küntz et al., Instiutte of Physics Publishing, 34 (2001) 2547–2554.

"*Concrete Test Methods*". Tentative Recommendations. RILEM. Materials and structures. (English translation) 7:291–296 (1972).

\* cited by examiner

TESTING PROCESS AND APPARATUS FOR DETERMINING ABSORPTION PROPERTIES OF POROUS SPECIMEN

RELATED APPLICATION

This application claims priority from Canadian patent application number 2,342,119, filed Mar. 23, 2001, the disclosure of which is incorporated by reference herein in its entirety.

FIELD OF THE INVENTION

The present invention relates to testing process and apparatus for determining absorption properties of a porous specimen, and more particularly to testing process and apparatus for automatic measurement of water absorption and characterization of the absorption capacities and properties of porous materials, for example construction materials such as concrete, mortar, brick, stone, bituminous coated material, plaster, etc.

BACKGROUND

Deterioration of construction works (bridges, viaducts, tunnels, roads . . . ) and of buildings is mainly due to water which seeps by capillarity in the construction materials such as brick, stone, concrete. The mechanisms responsible for the deterioration of building materials are largely mediated by water and have been much described in specialized literature. The conjugate action of mechanical and chemical damages arising for instance from freeze/thaw cycles, shrinkage-induced cracking, salt crystallization and leeching (dissolution, selective migration of chemical elements, re-crystallization), interactions between the elements in solution or in suspension in water such as sodium and chloride ions or $CO_2$ with the porous matrix or the framework, foam development, algae or fungi, may lead to rapid degradation of the bulk material properties of construction or building materials and significantly reduce the service life of the construction works. The durability of building structures is thus critically determined by the rate at which water and the many deleterious chemical agents it contains infiltrate and move through the porous structure. It is thus essential to quantify the absorption properties of the materials to estimate and eventually improve the durability of the construction works. This need, recognized very early, has motivated a very large number of studies since the beginning of the century and this effort is actually sustained.

One of the most currently used process for characterizing the absorption capacities of porous materials consists of measuring weight change in a specimen having an end brought in continuous contact with water. This process allows obtaining the quantity of water penetrating by capillarity in the material as a function of time. This process, generally called absorption test in the specialized literature, is classically used in construction engineering. It has been the object of many recommendations from different international organizations (see for example: "Standard Test Methods for Sampling and Testing Brick and Structural Clay Tile" ASTM, 2000, C67-99a, 1-10; "Concrete Test Methods", Tentative Recommendations, RILEM, 1972, Materials and structures, 7, 291–296) and has been described in numerous publications (see for example: "Water sorptivity of mortars and concretes: a review", C. Hall (1989), Magazine of concrete Research, 41, 51–61; "Barrier performance of concrete: A review of fluid transport theory", C. Hall (1994), Material and structures, 1994, 27, 291–306). In all of these documents, it is suggested to carry out the weighing operation manually. The sample or specimen is drawn out of the reservoir at a regular time interval, wiped to eliminate excess water at the surface of the test specimen, weighed on a precision scale, and then set back in contact with water. This protocol is easy to practice but presents many flaws that may critically affect the quality of the measurements. The absorption process must be stopped during the weighing operation: it is thus not a continuous type of measurement. The consequences of these repeated interruptions on the measurement of the absorption properties are particularly important in the first minutes of the test. A residual amount of water at the surface of the sample when it is weighed may be largely greater than the quantity of water really absorbed by the sample at the beginning of the test. It is worth mentioning that the above-cited documents provide no indication on a way of estimating or reducing this error. The fact that many manipulations are required to measure the quantity of absorbed water considerably reduces the frequency at which the measurements can be carried out.

The results of the absorption test, most often obtained over periods of one hour or less, are then extrapolated for the typically much longer times of the service life of the construction works and buildings using unsaturated flow theory, a description of which is given in the above-mentioned documents of C. Hall. The theoretical model, routinely used since about 20 years in construction engineering, predicts that the increase of the quantity of water absorbed by capillarity during the absorption test proportionally varies as $t^{1/2}$ (where t is the time during which the sample is in contact with water). The proportionality constant, called sorptivity, is generally interpreted as an intrinsic physical property of the material which characterizes its capacity to absorb water by capillarity. The fact that the content in water is initially null in the material is generally not considered (even though this condition is imposed) and the measurements carried out at the beginning of the test are neglected in the calculation of the sorptivity, as it appears from the above-mentioned documents of C. Hall and in "A water sorptivity test for mortar and concrete", B. B. Sabir et al., 1998, Materials and structures, 31, 568–574.

The unsaturated flow theory does not satisfactorily account for the infiltration process in porous milieu. The Applicant has discovered that the absorption capacities of porous materials are in fact largely higher than those predicted by the classical model. There is a need to improve the quality of the measurements of the water quantity absorbed by the material from the beginning of the absorption test. Likewise, there is a need to improve the absorption test to reach a correct estimate of the absorption capacities of construction materials.

The long time predictions of both the amount and the penetration depth of absorbed water based on the classical $t^{1/2}$ relation are generally underestimated. Because this may also apply to many deleterious chemical agents mediated by water, the consequences of water infiltration on the durability of building materials may also be dramatically underestimated. The experimental procedure should be improved to increase the number and accuracy of cumulative infiltration data, especially at short times, to allow more reliable estimates of the absorption properties of porous building materials.

SUMMARY

An object of the present invention is to provide testing process and apparatus which provide more reliable estimates of the absorption properties and behavior of porous materials in order to reach a better diagnostic on the durability of construction works.

Another object of the present invention is to provide testing process and apparatus which provide more accurate cumulative infiltration (water absorption) measurements even at the very beginning of the test.

Another object of the present invention is to provide testing process and apparatus allowing a continuous weighing of a porous specimen during water absorption.

Another object of the present invention is to propose testing process and apparatus for improving the estimation of the absorption properties of construction materials.

Another object of the present invention is to provide a testing process which can be practised in any office and laboratory and by any service involved in the design, construction or restoration of construction works and buildings.

Another object of the present invention is to provide such a testing process and apparatus which are applicable for unsaturated porous materials such as concrete, brick, stone, bituminous coated material, plaster, and the like.

According to the present invention, there is provided a testing process for determining absorption properties of a porous specimen, comprising: bringing the porous specimen in a predetermined state of contact with the body of water for inducing water absorption in the porous specimen; monitoring a weight of the porous specimen for a predetermined time period once the contact is established to produce weight data over time; maintaining the predetermined state of contact substantially constant during the predetermined time period; and determining the absorption properties of the porous specimen as a function of the weight data over time.

According to the present invention, there is also provided a testing apparatus for determining absorption properties of a porous specimen, comprising: a reservoir adapted to hold a body of water; a support extending over the reservoir, for hanging the porous specimen; a means for effecting a relative displacement of the reservoir and the support toward each other to bring the porous specimen in a predetermined state of contact with the body of water for inducing water absorption in the porous specimen; a means for maintaining the state of contact substantially constant during a predetermined time period; and a weighing means for measuring a weight of the porous specimen hanged by the support during the predetermined time period and providing weight data over time based on the weight; whereby the absorption properties are determinable as a function of the weight data.

Preferably, the testing apparatus also comprises a computer means connected to the weighing means, for determining the absorption properties as a function of the weight data over time.

The following provides a non-restrictive summary of certain features of the invention which are more fully described hereinafter.

With the testing apparatus according to the present invention, significant measurements of the quantity of water absorbed by the test specimen can be obtained as soon as the process begins. The frequency of the measurements during the test can be higher than in conventional process.

The analysis of the data resulting from the absorption measurements preferably uses an anomalous diffusion model developed by the Applicant to quantify the absorption properties of the porous materials subjected to testing with the present invention.

In short, the apparatus according to the present invention has a weighing device provided with a sensor to which the test specimen is hung. A water reservoir is provided for controlled immersion of a lowermost end of the specimen. An electronic device converts the analog signal produced by the sensor into a digital signal transmitted to a computer for data storage and analysis. A software component installed on the computer controls the test operations and analyzes the measurement data according to a predetermined model, preferably an anomalous diffusion model as developed by the Applicant. The weighing device, the water reservoir and the electronic device can be assembled on a rigid frame. The computer can be a PC type computer and may be provided separately from the testing apparatus.

The operation of the apparatus is based on the following general principles. The absorption of water by the specimen and the weighing are carried out simultaneously. The apparatus thus allows to record continuously the weight variations of the specimen during the absorption process. The weighing device is stationary, so as to avoid perturbations in the measurements which would be caused by a displacement of the sensor when the specimen is brought in contact with the water surface. The contact is preferably established by displacing vertically the reservoir which rests over a mobile platform. The water level is kept constant in the reservoir by permanently supplying the reservoir with water during the test. The water renewal in the reservoir allows, among other things, to keep the liquid at a constant temperature and thus to reduce experimental biases that could result from a change of physical properties.

BRIEF DESCRIPTION OF THE DRAWINGS

A detailed description of preferred embodiments will be given herein below with reference to the following drawings, in which like numbers refer to like elements.

DETAILED DESCRIPTION OF THE PREFERRED EMBODIMENTS

Figure 1:
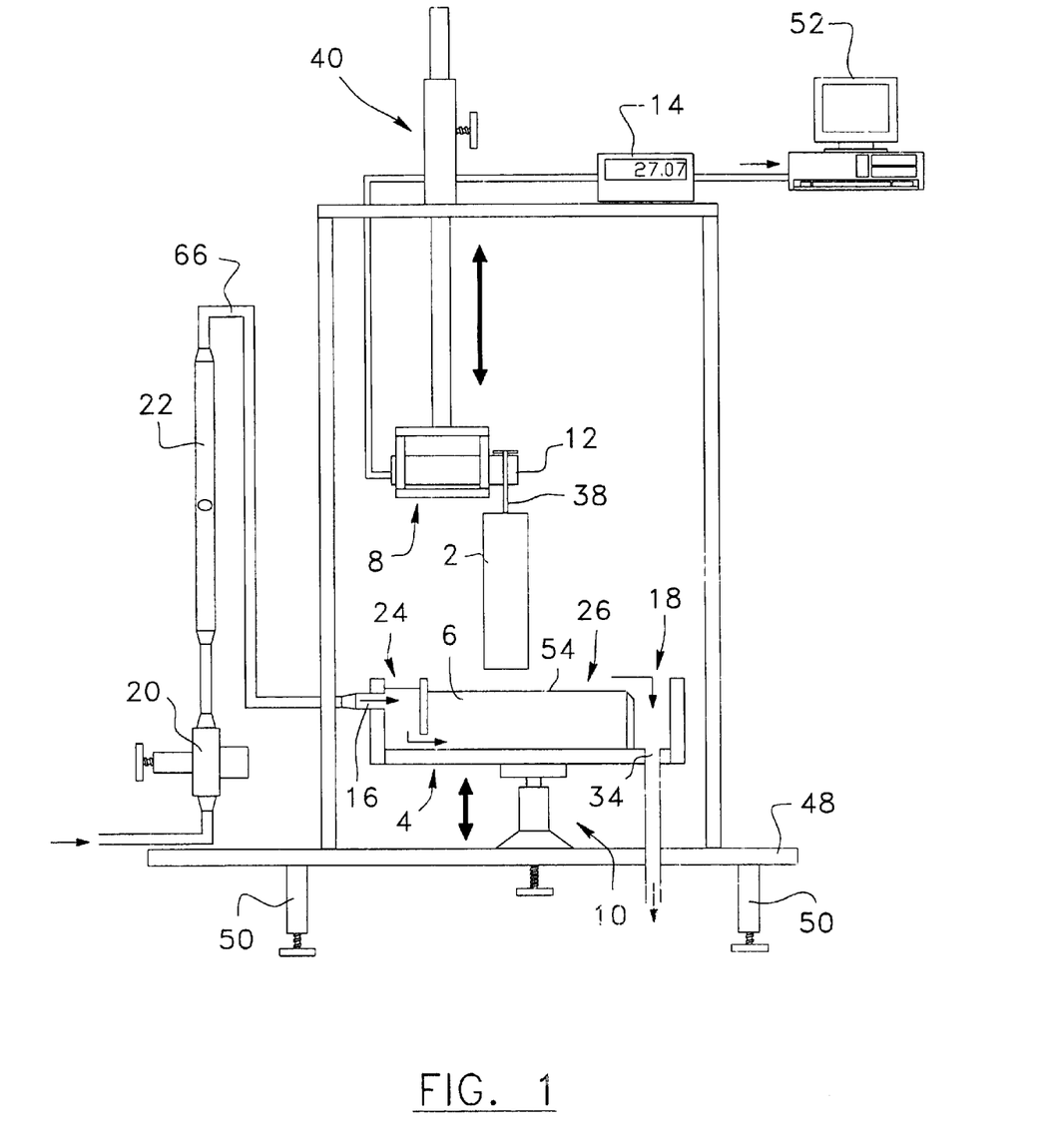
FIG. 1 is a schematic view of a testing apparatus according to the present invention.

Referring to FIG. 1, there is shown a testing apparatus for determining absorption properties of a porous specimen 2 according to the present invention. The apparatus has a reservoir 4 adapted to hold a body of water 6. A support 8 extends over the reservoir 4, for hanging the specimen 2. The apparatus has a device for controllably effecting a relative displacement of the reservoir 4 and the support 8 toward each other to bring the specimen 2 in a predetermined state of contact with the body of water 6 for inducing water absorption in the porous specimen 2. The device can take different configurations, one of which consists of a jack arrangement 10 under the reservoir 4 to lift it until the lower end of the specimen 2 is immersed at the surface level of the body of water 6, as in the illustrated case. The apparatus has also a device for maintaining the state of contact substantially constant during a predetermined testing time period, which device can be conveniently embodied by a water circulation circuit to maintain the surface level of the body of water 6 constant as more fully described hereinafter. A weighing device for example made of a load cell 12 and an analog-digital meter 14 is provided for measuring a weight of the specimen 2 hanged by the support 8 during the testing time period and providing weight data over time based on the weight so measured. As it will be seen hereinafter, the absorption properties can be determined as a function of the weight data.

The reservoir has a water supply inlet 16 and a water overflow 18. A pressure regulator 20 and a flow meter 22 may be used for regulating water supplied to the reservoir 4 through the water supply inlet 16.

Figure 3A:
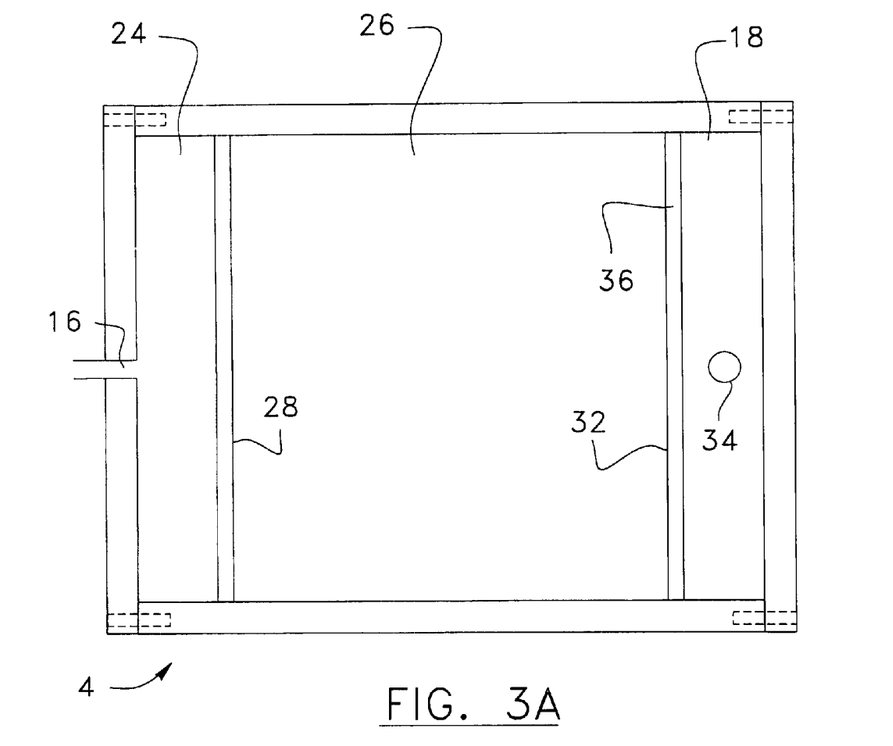
FIGS. 3A and 3B are top and side schematic views of a reservoir in a testing apparatus according to the present invention.
Figure 3B:
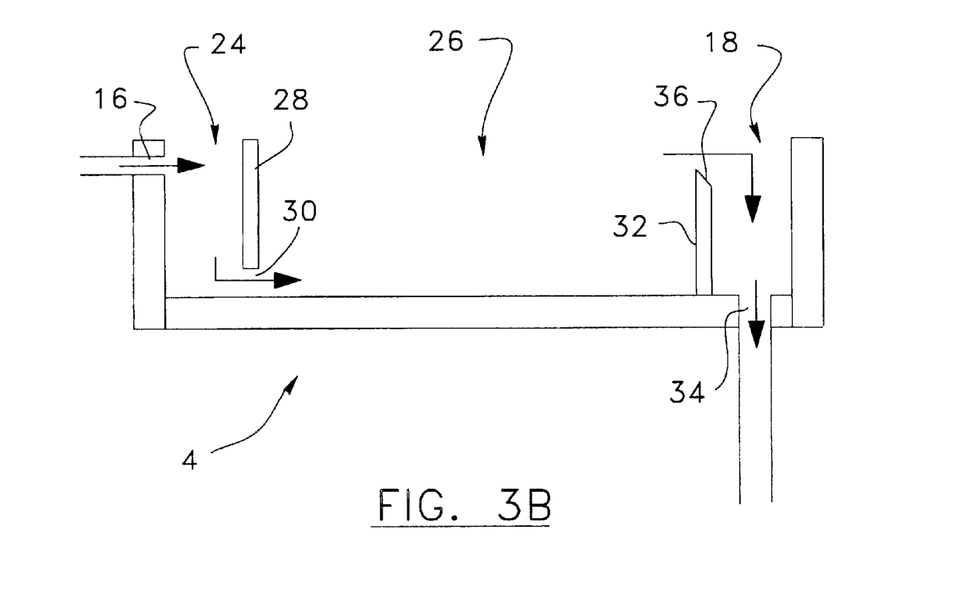

Referring to FIG. 3B, the reservoir 4 is preferably divided into chambers, one forming a water supply chamber 24 provided with the water supply inlet 16, and another one forming a measurement chamber 26 provided with the water overflow 18 and adapted to receive the specimen 2 (see FIG. 1). The water supply and the measurement chambers 24, 26 are separated by a partitioning wall 28 extending in front of the water supply inlet 16 at a distance from it and upwardly projecting out of the body of water 6 (see FIG. 1). The wall 28 has a bottom opening 30 for water communication between the water supply and measurement chambers 24, 26. The water overflow 18 may also be in the form of a chamber on a side of the measurement chamber 26 opposite to the water supply chamber 24. The overflow and measurement chambers 18, 26 are separated by a partitioning wall 32 having a height controlling a surface level of the body of water 6 in the measurement chamber 26. The overflow chamber 18 has a drain 34 for escape of excess water out of the reservoir 4. Preferably, the partitioning wall 32 separating the overflow and measurement chambers 18, 26 has an upper bevelled face 36 provided with an absorbent material (not shown) such as felt or cotton of approximated 1 mm thick, whose function is to prevent the formation of an unstable water ripple at the wall-liquid interface.

Referring back to FIG. 1, a permanent water circulation is established in the reservoir 4 in order to maintain the water level 54 constant during the test. The reservoir is supplied in water by the inlet 16 located, in the illustrated embodiment, at an upper portion of the supply chamber 24. The water flows down in the supply chamber 24 before passing into the measurement chamber 26 through the opening 30 which is relatively narrow to reduce swirl in the reservoir 4. This circulation mode facilitates the suppression of eventual air bubbles, slows down the fluid so as to obtain a laminar flow and eliminates ripples in the measurement chamber 26. An amount of the water contained in the measurement chamber 26 is absorbed by capillarity by the specimen 2. The excess water is continuously drained toward the overflow chamber 18 and escapes through the opening 34 preferably having a large diameter located at the bottom of the overflow chamber 18. The depth of the reservoir 4 can be small, e.g. 5 cm. The measurement chamber 26 forms the largest part of the reservoir 4, for example 14×17 cm$^2$, and can receive samples having a section reaching 100 cm$^2$ (10 cm×10 cm). As the volumes of water involved in the process are reduced, the manipulation of the reservoir 4 is easy. Polymethyle methacrylate (PMMA) or any other rigid plastic material can be used for the construction of the reservoir 4.

The reservoir 4 can be supplied from the municipal water distribution network. The pressure regulator 20 and the flow meter 22 installed on the supply pipe 66 upstream from the reservoir 4 control the water flow. A typical water flow can be in the order of 10 cm$^3$/s. Control of the pressure regulator 20 and the flow meter 22 can be achieved by a computer 52 or in a manual fashion as illustrated. The section of the inlet opening 16 of the supply chamber 24 can be larger than the section of the supply pipe 66 to prevent the generation of bubbles at the inlet 16 of the reservoir 4.

The load cell 12 mounted on the support 8 is provided with a bracket 38 adapted to support the specimen 2 during the testing time period. A height adjustment device 40 is preferably provided for selectively rising and lowering the support 8 over the reservoir 4.

The bracket 38 may be arranged to receive a sample having a prismatic or cylindrical shape with a variable section. It should maintain the sample in vertical position along the axis of the weighing device. The bracket 38 may be formed of an upper fastener element for attachment to the load cell 12 and a lower clamping element arranged to immobilize the sample, with the upper portion the sample pressing against a plate of a few provided with nibs of a few millimeters of length. This plate is used as a reference surface and ensures that the sample is vertical and placed in the axis of the weighing device. The nibs allow a free circulation of air between the plate and the upper face of the sample and prevent any concentration on the edges of the sample.

Figure 2:
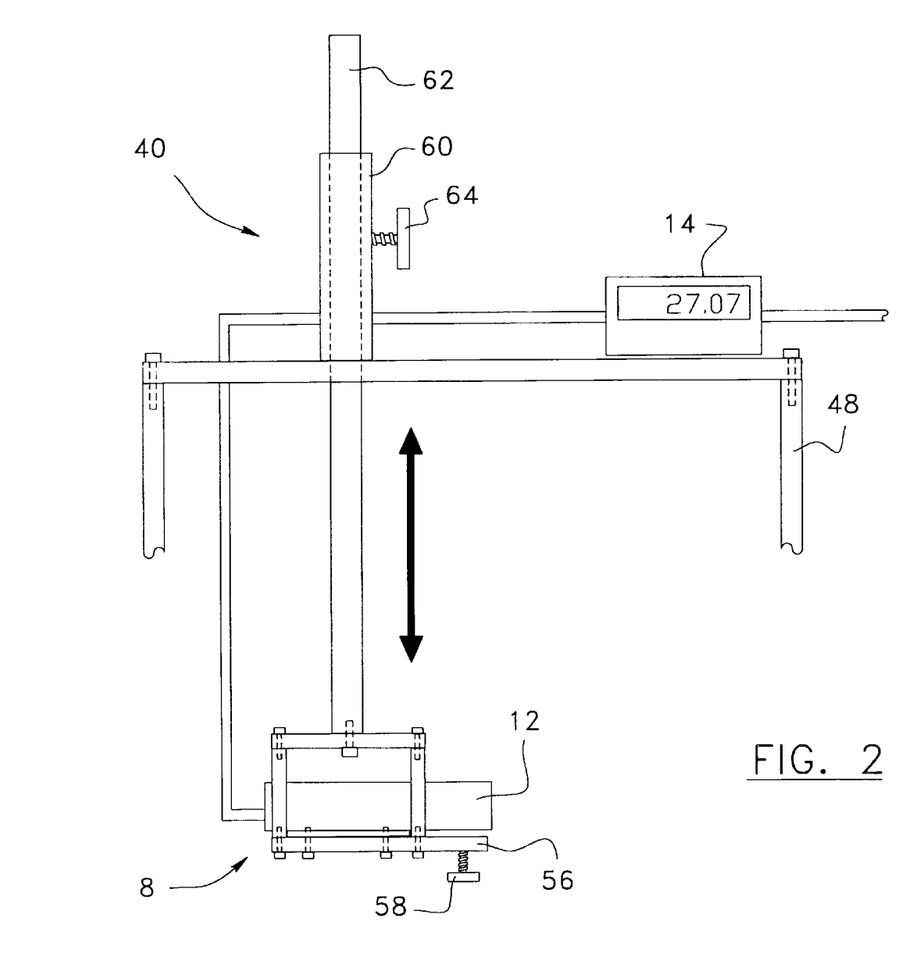
FIG. 2 is a schematic view of a weighing device in a testing apparatus according to the present invention.

Referring to FIG. 2, the height adjustment device 40 may be formed of a shaft 62 vertically sliding in a sleeve 60 secured to the frame 48 of the apparatus and provided with a locking screw 64 to allow the positioning of the sensor-sample set at a variable height according to the size of the test specimen 2, for example over a 30 cm course. A template can be used for the precise adjustment of the lower face of the sample with respect to the water level 54 in the reservoir 4.

Referring back to FIG. 1, the reservoir 4, the support 8 and the weighing device can be mounted on a supporting frame 48 with adjustable legs 50 for placing the platform which supports the reservoir 4 in a horizontal plane. A bubble level disposed on top of the apparatus may be used to facilitate the adjustment at the horizontal. The materials selected for the construction of the frame 48 are preferably sufficiently rigid to support the progressive increase of the weight of the specimen 2 during the test without deformation. It can be made for example of stainless steel, plastic material or an aluminum alloy. Each leg 50 is preferably provided with a rubber pad (not shown) for the purpose of absorbing high frequency vibrations that could arise from other apparatuses located near the apparatus or from the ventilation system of the building where the test is carried out. The suppression of high frequency vibrations allows to eliminate perturbations that could affect the measurements.

The jack arrangement 10 is arranged to selectively lift and lower the reservoir 4 respectively toward and away from the support 8 between a position where the specimen 2 hangs over and outside the body of water 6 (as illustrated) and a position where the specimen 2 is in the state of contact with the body of water 6.

Figure 4:
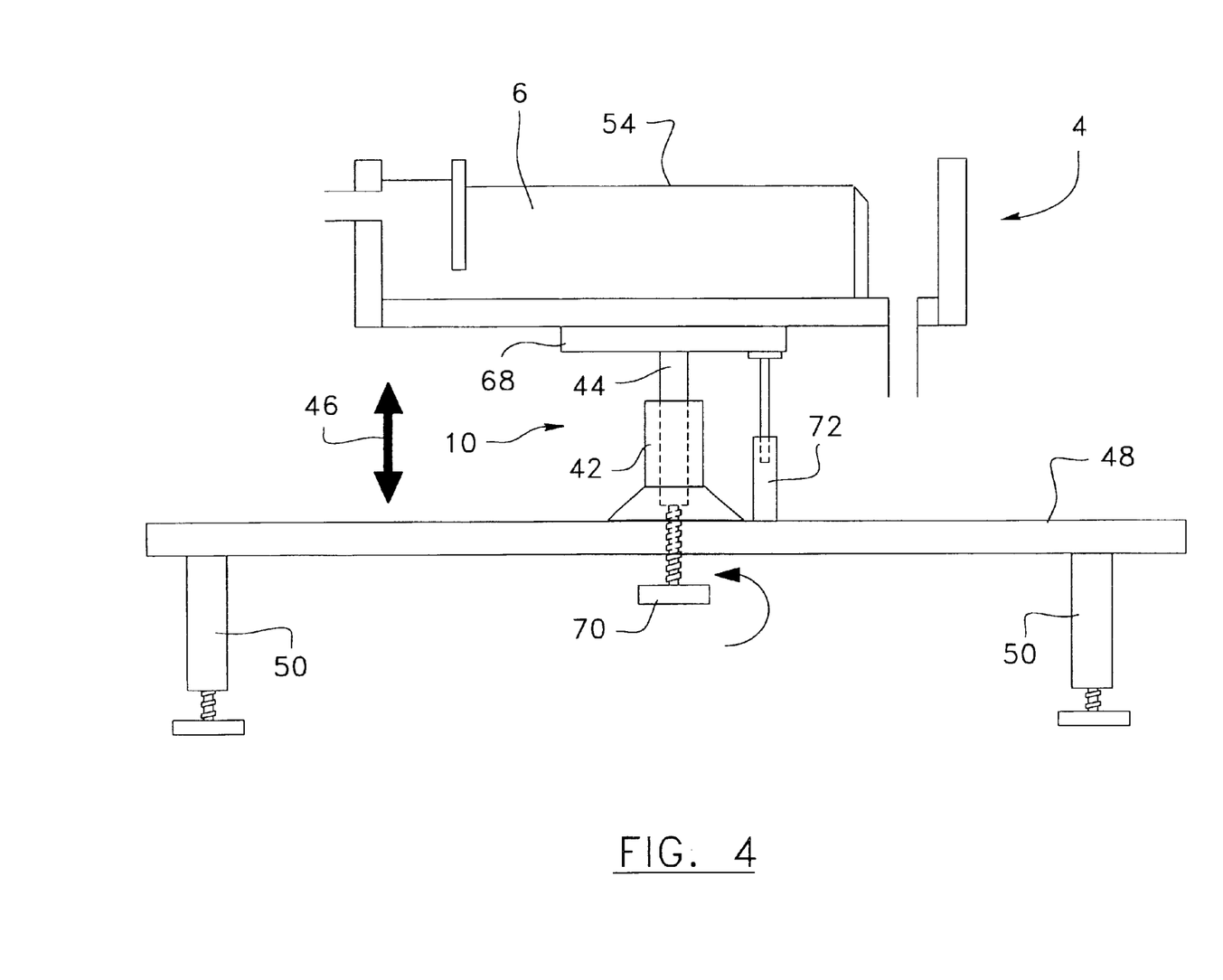
FIG. 4 is a schematic view of a lifting mechanism in a testing apparatus according to the present invention.

Referring to FIG. 4, the jack arrangement 10 may conveniently be made of a jack 42 mounted on the frame 48 and having a mobile shaft 44 moving along a vertical course as depicted by arrow 46. The reservoir 4 is supported by a mobile platform 68 which vertically moves with the shaft 44 for establishment of the contact between the lower face of the specimen 2 and the water surface 54 at the beginning of the test. The jack arrangement 10 can be operated manually by means of a screw 70 located under the frame 48, or through an appropriate motorized arrangement (not shown) which can be controlled by the computer 52. A guiding arrangement 72 restricts operation of the jack 42 vertically and prevents the platform 68 from rotating. A typical total course of the lifting device is, for example, approximately 10 mm. The displacement speed should be sufficiently slow to avoid undesired ripples at the surface of the body of water 6 and water spilling which would temporarily change the water level 54 in the reservoir 4.

Referring again to FIG. 1, the weight data provided by the weighing device are transmitted to the computer 52 which determine the absorption properties as a function of the weight data over time. The computer 52 can be provided with a data acquisition circuit for acquiring the weight data, a processing circuit for processing the weight data, and an analyzing circuit for analyzing the weight data based on the desired model (preferably the anomalous diffusion model proposed by the Applicant) and communicating data indicative of the absorption properties.

According to the testing process of the present invention, the specimen 2 is brought in a predetermined state of contact with the body of water 6 for inducing water absorption in the specimen 2. The weight of the specimen 2 is monitored for a predetermined testing time period once the contact is established, to produce weight data over time. The predetermined state of contact is maintained substantially constant during the testing time period. The absorption properties of the specimen 2 are determined as a function of the weight data over time as produced during the monitoring.

For a capillary rise absorption test, the contact is preferably limited to a bottom portion of the specimen 2 with a surface level 54 of the body of water 6.

Typically but not restrictively, the testing apparatus can be used to test samples having a length of 5 to 30 cm for a maximum weight of 1.5 kg and for a useful absorption section that may vary from 10 to 100 cm$^2$. The apparatus is designed for carrying out several measurements per second. The size of the apparatus (frame 48 and reservoir 4) and the capacities of the measuring instruments (load cell 12 and meter 14) can be changed if samples having a larger size must be measured.

The load cell 12 may operate either in torsion (e.g. TEDEA Huntleigh sensor, model 1030) or in traction-compression. The meter 14 can conveniently be embodied by a Series 2000 instrument from the company Daytronic, equipped with a RS232 output and allowing one measurement per second. Other kinds of sensors capable of weighing the specimen 2 and appropriate meters can be used if desired. The load cell 12 must support the combined weights of the bracket 38 and the saturated porous specimen 2 held by the bracket 38. With the above kind of sensor, the maximal capacity is 2 kg (20 Newtons) with a 0.01 g resolution. The dry weight of the specimens should not exceed 1.5 kg in this case. A sensor operating on a larger loading scale may be used for heavier specimens.

Referring to FIG. 2, the weighing device is provided with a stationary mechanical stop 56 mounted on the frame 48 to prevent the load cell 12 from suffering damages that could result should its capacity be exceeded during the manipulation. A removable mechanical stop 58 may be provided to block the load cell 12 in neutral position during the installation of the specimen 2.

Referring to FIG. 1, various instruments can be added to increase the quality of the results. The water level 54 in the reservoir 4 can be measured continuously on a 1/100 mm scale by means of a displacement sensor. A thermometer and an electronic hydrometer can be installed to measure the environmental conditions around the sample during the test. The measurements provided by these instruments are recorded by the computer 52 and can eventually be used to correct the absorption data during the data analysis.

The computer 52 has two main functions. One is the control of the test parameters, and the other is the acquisition of the digital signal, the processing and analyzing of the measurements. The analysis of the data is preferably based on the theoretical anomalous diffusion model described hereinafter. An interface such as Easyest LX (trademark) from the company Keithley Asyst can be used for the recordation of the raw data provided by the meter 14 and the other possible control instruments. The control of the test parameters can be manual. The absorption test data are processed later using appropriate software programs. The processing allows to quantify the absorption capacities. The control of the test parameters and the data acquisition can be achieved as follows. The parameters of the test and the characteristics of the test specimen 2 are entered, e.g. test name, date, characteristics of the sensor (gain, maximum capacity, etc.), nature of the material, weight and size of the specimen, absorption section, porosity, duration and acquisition frequency of the test, water flow and pressure, ambient temperature and relative humidity, etc.

The measurement line is initialized and tested. An alarm is activated to report any sensor overload. The control of the lifting device 10, water supply valves and other possible devices can be achieved through the computer software.

The system is placed in acquisition mode. The data provided by the meter 14 and the possible control instruments (temperature, relative humidity degree, flow, etc.) are recorded. A real time representation of the absorption data on the computer's display can be carried out to visually control the progress of the test.

The data processing consists of essentially converting the raw data (in mv) provided by the acquisition system in grams or in volume per unit surface according to the desired representation type, correcting the raw data from any environmental data such as the temperature or the humidity degree that could have affected the absorption process or changed the properties of the liquid so as to reduce the uncertainty on the measurement if necessary, and representing the evolution of the quantity of water absorbed as a function of time (e.g. in a 2D diagram). The test parameters and the characteristics of the test specimen entered at the previous step are used for this purpose. Each step of the process can be saved.

The anomalous diffusion model in unsaturated porous media developed by the Applicant and which the computer 52 preferably applies can be summarized as follows.

The theoretical model is based on the assumption of a non-Fickian diffusion process for infiltration. For simplicity, the analysis is restricted to one-dimensional flow along the x-direction. The exponent ½ in $\phi = x/t^{-1/2}$ is a direct consequence of Fick's diffusion hypothesis. In order to decouple time and space derivatives, assume the following modified Fick's equation:

$$q = -D(\theta)\left(\frac{\partial \theta}{\partial x}\right)^n \quad (1)$$

i.e. the volumetric moisture flow q is now a function of the moisture gradient at the power n, with n real.

Combining equation (1) with the conservation of mass gives the nonlinear diffusion equation:

$$\frac{\partial \theta}{\partial t} + \nabla q = 0 \quad \text{or} \quad \frac{\partial \theta}{\partial t} - \frac{\partial}{\partial x}\left[D(\theta)\left(\frac{\partial \theta}{\partial x}\right)^n\right] = 0 \quad (2)$$

Developing (2), and assuming that $D(\theta)$ is a function of $\theta$ only, there is obtained:

$$\frac{\partial \theta}{\partial t} - \frac{dD(\theta)}{d\theta}\left(\frac{\partial \theta}{\partial x}\right)^{n+1} - nD(\theta)\left(\frac{\partial \theta}{\partial x}\right)^{n-1}\frac{\partial^2 \theta}{\partial x^2} = 0. \quad (3)$$

Instead of the scaling factor $\phi = x/t^{1/2}$ of the normal diffusion equation, assume that $\phi$ is a function of the single variable $\phi^* = x/t^\alpha$, with $\alpha$ real, and define the derivatives $\theta' = d\theta/d\phi^*$ and $\theta'' = d^2\theta/d\phi^{*2}$. Application of the transformation $\phi^* = x/t^\alpha$ reduces equation (3) to the following ordinary differential equation:

$$\theta'' + \frac{1}{nD(\theta)}\frac{dD(\theta)}{d\theta}(\theta')^2 + \frac{\alpha}{n}\frac{\phi^*}{D(\theta)}(\theta')^{-n+2} = 0 \quad (4)$$

provided that:

$$t = t^{\alpha(n-1)} \quad \text{i.e.} \quad n = \frac{1}{\alpha} - 1. \quad (5)$$

For the case of one-dimensional absorption where $\theta = \theta_0$ at $x > 0$ at $t = 0$ and $\theta = \theta_1$ at $x = 0$ at $t > 0$, the boundary conditions which apply to (4) are:

$$\begin{cases} \theta = \theta_1 & \text{at } \phi^* = 0 \\ \theta = \theta_0 & \text{for } \phi^* \to \infty \end{cases} \quad (6)$$

Because equation (4) with boundary conditions (6) has only one solution $\theta = f(\phi^*)$, the absorption profiles measured at different times must be related by a simple $t^\alpha$ transformation provided that the application of the previous analysis to infiltration is valid, i.e. the profiles are expected to collapse on a single master curve $\theta = f(\phi^*)$ when plotted as a function of $\phi^*$. The moisture diffusivity can be easily determined by integrating (4) with respect to $\phi^*$ using the boundary conditions (6). This yields:

$$D(\theta) = \frac{-1}{n+1}\left(\frac{d\theta}{d\phi^*}\right)^{-n}\int_{\theta_0}^{\theta}\phi^* d\theta. \quad (7)$$

The cumulative infiltration I is given by:

$$I = \int_{\theta_0}^{\theta_1} x d\theta = t^\alpha \int_{\theta_0}^{\theta_1} \phi^* d\theta = S^* t\alpha \quad (8)$$

with S* constant.

The data analysis has three basic elements to which additional tools can be added during the development. A first element is a data smoothing function for reducing the noise in the measurements. This tool is required when the sampling frequency is high. A second element is a regression in power law in order to find the exponent $\alpha$ and the proportionality constant. A third element is a derivative function to determine the fluctuations of the exponent $\alpha$, quantify the error on this parameter and determine the instantaneous absorption rate.

A possible extension of the data analysis may consist in creating a database which will get richer at each test and that may be used as a comparison base. In particular, it enables to determine if the absorption properties of the specimen meet the regulations in force according to the nature of the material and the obtained results.

An example of the main steps of the measurement process and the absorption property analysis of a porous material as achieved in laboratory using the apparatus according to the invention is described hereinafter. The characterization of the absorption properties must be achieved on isotropic homogeneous samples. However, the effect of the joints (contact brick-concrete, concrete-cement for repair) or cracks on the absorption capacities of construction materials can be studied.

In regard with the preparation of the test specimen, the technician arranges it so that its lower and upper surfaces are parallel. To ensure the unidimensional character of the test, the technician will verify that the section of the test specimen is constant over its whole length. The dimensions of the specimen are measured as accurately as possible, preferably with a sliding caliper so as to obtain a precise estimation of the effective absorption surface.

To ensure a reproducibility of the testing conditions, the specimen is heated at a controlled temperature to allow complete and uniform drying and is stored in a climatic chamber at controlled temperature and relative humidity until it is used. The dried sample is weighed before the test. The lateral surfaces of the sample are then coated with a sealing product (tar, paraffin, etc.) in order to prevent any water infiltration from the sides, and the sample is weighed again.

The reservoir 4 is connected to a suitable water supply and then progressively filled in down position. The water flow is adjusted so that the flow is laminar.

The horizontality of the apparatus is verified and the level is corrected if necessary. The sensor 12 is initially blocked in neutral position using the movable stop 58. The specimen is placed in the bracket 38. The bracket-sample set is hanged on the sensor 12 and its height is adjusted at about 5 mm above the water surface 54 of the reservoir 4 still in down position. The removable stop 58 which maintains the sensor 12 in neutral position is removed. The sensor 12 which supports the load made of the bracket 38 and the dry sample 2 is initialized to zero.

The software process is initiated. A first reading of the signal provided by the meter 14 is achieved to verify the operation of the various elements of the measurement device. The testing parameters are then entered. The measurement instruments are initialized and the computer 52 is finally set in acquisition mode.

The reservoir 4 is progressively lifted by means of the jack arrangement 10 until the lower end of the specimen 2 is brought just in contact with the water level 54. Recordation of the signal provided by the meter 14 begins as soon as the reservoir 4 is immobilized in its final position. The duration of the test may vary from a few minutes to several hours depending on the objectives sought. The electric signal provided by the meter 14 is converted in grams and projected in real time on the computer's display as a function of time. The computer simultaneously records the time elapsed in seconds, the signal from the meter 14 in microvolts, and all the data relative to the test provided by the various instruments such as the pressure regulator 20, the displacement sensor, the thermometer and the hydrometer.

The bracket 38 holding the specimen can be constructed to allow measurement of absorption properties of non-cohesive materials such as soils. The samples can be placed in rigid sleeves closed at the base by a porous membrane.

The sides of the frame 48 can be closed so as to create a sealed enclosure in which the temperature and the relative humidity can be accurately controlled. Measurements of the drying process for the preparation of the specimen could be achieved in such an arrangement. The reservoir 4 can be supplied in water from a container independent from the water distribution network, provided with a suitable pump having a steady flow. The computer 52 can be replaced by a simple memory device for the recordation of raw data, the data analysis being achieved later. The same meter 14 may be used to process weight data coming from several reservoirs simultaneously. Depending on the construction of the apparatus, the contact could be established either by moving down the specimen 2 into the body of water 6 instead of lifting the reservoir 4, or by a combined displacement of both. The apparatus according to the present invention can be easily arranged to perform other types of tests if desired, such as one in which the specimen needs to be completely immersed in the body of water 6. The model implemented in the computer 52 for analyzing the data can be also modified to account for other parameters depending on the nature of the test. The state of contact between the specimen 2 and the body of water 6 can also be maintained for example using equipment and measuring instruments causing the reservoir 4 and/or the specimen 2 to move as necessary to follow a change in the water level 54. Therefore, while embodiments of this invention have been illustrated in the accompanying drawings and described above, it will be evident to those skilled in the art that changes and modifications may be made therein without departing from the essence of this invention. All such modifications or variations are believed to be within the scope of the invention as defined by the claims appended hereto.

What is claimed is:

1. A testing process for determining absorption properties of a porous specimen, comprising:
   bringing the porous specimen in a predetermined state of contact with a body of water for inducing water absorption in the porous specimen;
   monitoring a weight of the porous specimen for a predetermined time period once the contact is established to produce weight data over time;
   maintaining the predetermined state of contact substantially constant during the predetermined time period; and
   determining the absorption properties of the porous specimen as a function of the weight data over time.

2. The testing process according to claim 1, wherein the step of bringing comprises limiting the contact to a bottom portion of the porous specimen with a surface level of the body of water.

3. The testing process according to claim 2, wherein the step of maintaining comprises:
   adding water to the body of water; and
   discharging an overflow of water from the body of water so that the surface level of the body of water remains substantially constant during the predetermined time period.

4. The testing process according to claim 3, wherein the step of maintaining comprises producing a continuous steady-state flow of water in the body of water during the predetermined time period.

5. The testing process according to claim 4, comprising an additional step of preparing the porous specimen prior to the step of bringing, the step of preparing comprising applying an impermeable coating on side faces of the porous specimen adjacent to a bottom face of the porous specimen involved in the contact with the body of water.

6. The testing process according to claim 5, wherein the step of preparing comprises drying up the porous specimen prior to the step of bringing.

7. The testing process according to claim 5, wherein the step of bringing comprises raising the body of water toward the porous specimen until the contact is established.

8. The testing process according to claim 5, wherein the predetermined time period starts as soon as the contact is established.

9. The testing process according to claim 8, wherein the predetermined time period lasts at least one hour.

10. The testing process according to claim 8, wherein the step of monitoring comprises measuring the weight of the porous specimen at a predetermined time rate during the predetermined time period, the weight data being formed of weight measurements resulting from the step of measuring.

11. The testing process according to claim 1, wherein the step of determining comprises processing the weight data based on an anomalous diffusion model.

12. A testing apparatus for determining absorption properties of a porous specimen, comprising:
   a reservoir adapted to hold a body of water;
   a support extending over the reservoir, for hanging the porous specimen;
   a means for controllably effecting a relative displacement of the reservoir and the support toward each other to bring the porous specimen for predetermined state of contact with the body of water for inducing water absorption in the porous specimen;
   a means for maintaining the state of contact substantially constant during a predetermined time period; and
   a weighing means for measuring a weight of the porous specimen hung by the support during the predetermined time period and providing weight data over time based on the weight;
   whereby the absorption properties are determinable as a function of the weight data.

13. The testing apparatus according to claim 12, wherein:
   the reservoir has a water supply inlet and a water overflow; and
   the means for maintaining comprises a means for regulating water supplied to the reservoir through the water supply inlet.

14. The testing apparatus according to claim 13, wherein the reservoir comprises a water supply chamber provided with the water supply inlet, and a measurement chamber provided with the water overflow and adapted to receive the porous specimen, the water supply and the measurement chambers being separated by a partitioning wall extending in front of the water supply inlet at a distance therefrom and upwardly projecting out of the body of water, the wall having a bottom opening for water communication between the water supply and measurement chambers.

15. The testing apparatus according to claim 14, wherein the water overflow comprises an overflow chamber on a side of the measurement chamber opposite to the water supply chamber, the overflow and the measurement chambers being separated by a partitioning wall having a height controlling a surface level of the body of water in the measurement chamber, the overflow chamber having a drain for escape of excess water out of the reservoir.

16. The testing apparatus according to claim 15, wherein the partitioning wall separating the overflow and the measurement chambers has an upper bevelled face provided with an absorbent material.

17. The testing apparatus according to claim 13, wherein the water supply inlet is provided with a pressure regulator and a flow meter.

18. The testing apparatus according to claim 12, wherein the weighing means comprises a load cell mounted on the support, the load cell being provided with a bracket adapted to support the porous specimen during the predetermined time period.

19. The testing apparatus according to claim 18, wherein the weighing means further comprises a metering circuit connected to the load cell and producing the weight data as a function of the weight measured by the load cell.

20. The testing apparatus according to claim 12, further comprising a height adjustment means for selectively rising and lowering the support over the reservoir.

21. The testing apparatus according to claim 12, wherein the means for effecting comprises a means for selectively lifting and lowering the reservoir respectively toward and away from the support between a position where the porous specimen hangs over and outside the body of water and a position where the porous specimen is in the state of contact.

22. The testing apparatus according to claim 21, wherein the means for selectively lifting and lowering comprises a jack extending under the reservoir and operating along a vertical course.

23. The testing apparatus according to claim 12, further comprising a frame supporting the reservoir, the support and the weighing means, the frame having adjustable legs.

24. The testing apparatus according to claim 12, further comprising a computer means connected to the weighing means, for determining the absorption properties as a function of the weight data over time.

25. The testing apparatus according to claim 24, wherein the computer means comprises a data acquisition circuit for acquiring the weight data, a processing circuit for processing the weight data, and an analyzing circuit for analyzing the weight data based on a predetermined model and communicating data indicative of the absorption properties.

26. The testing apparatus according to claim 25, wherein the predetermined model is an anomalous diffusion model.

* * * * *